United States Patent [19]

Potter et al.

[11] Patent Number: 5,747,056
[45] Date of Patent: May 5, 1998

[54] PESTICIDE COMPOSITIONS CONTAINING MUSTARD BRAN

[75] Inventors: John W. Potter, Ridgeville; Mikio Chiba, St. Catharines, both of Canada

[73] Assignee: Her Majesty in right of Canada as represented by the Minister of Agriculture and Agri-Food, Ottawa, Canada

[21] Appl. No.: 544,614

[22] Filed: Oct. 18, 1995

[51] Int. Cl.$^6$ ................................................. A01N 25/10
[52] U.S. Cl. ........................ 424/410; 424/405; 424/409
[58] Field of Search ................................ 424/405, 409, 424/410

[56] References Cited

U.S. PATENT DOCUMENTS

| | | | |
|---|---|---|---|
| 3,205,129 | 9/1965 | Kenaga et al. | 167/22 |
| 5,023,105 | 6/1991 | Warseck | 426/650 |

FOREIGN PATENT DOCUMENTS

| | | |
|---|---|---|
| 0383462 | 8/1990 | European Pat. Off. . |
| 3432555 | 3/1986 | Germany . |
| 0314231 | 7/1956 | Sweden . |

OTHER PUBLICATIONS

Ellenby, C., (1945), Annals of Applied Biol., v. 32, pp. 67–70.
Ellenby, C., (1951), Annals of Applied Biol., v. 38, pp. 859–875.
Akhtar, M. and Mahmood, I., (1994), Bioresource Technology, v. 48, pp. 189–201.
Singh, S.P. et al., (1980), Nematol. Medit., v. 8, pp. 193–198.
Singh, S.P. et al., (1993), Nematol. Medit., v. 11, pp. 115–118.
Toxicants Occurring Naturally in Foods: Spices and Flavors, Hall p. 166, 1966.
Journal of Economic Entomology, vol. 88, No. 5, Oct. 1, 1995, pp. 1192–1196.
Chemical Abstracts, vol. 108, No. 1, Jan. 4, 1988, Abstract No. 145313: FH Shah et al, *Comparison of Various Fractions of Mustard and Rape Seeds for their Amenability to Detoxification*.
Chemical Abstracts, vol. 89, No. 17, Oct. 23, 1978, G. Vangheesdaele et al *Origin and Role of Iron and Copper During the Preparation of the Dijon Mustard Paste*.
Database Cropu, Abstract 95–84011: SA Tiyagi et al, *Efficacy of Oil–Seed Cakes Against Plant Parastic Nematodes and Soil–Inhibiting Fungi on Mungean and Chickpea*.
Database Cropu, Abstract 94–87764: M. Akhtar et al, *Potentiality of Phytochemicals in Nematode Control: A Review*.
Chemical Abstracts, vol. 88, No. 23, Jun. 5, 1978, Abstract No. 165440: M. Alam et al, *Persistent Action of Oil Cakes and Nematicides on the Population of Nematodes in Field*.
Kleeberg et al DE4327792 Apr. 6, 1995.
Concannope WO9401121 Jan. 20, 1994.
Suntory, Ltd. JP5200/023 Jan. 6, 1977.

*Primary Examiner*—Neil S. Levy
*Attorney, Agent, or Firm*—Dinsmore & Shohl LLP

[57] ABSTRACT

The invention provides pesticide precursor compositions comprising bran from a mustard of the genus Brassica and methods for controlling soil pests by application of the pesticide precursor compositions to the soil. The invention further provides pesticides comprising aqueous suspensions or extracts of mustard bran.

10 Claims, No Drawings

PESTICIDE COMPOSITIONS CONTAINING MUSTARD BRAN

FIELD OF THE INVENTION

The present invention relates to compositions and methods for controlling pests. More particularly, the invention relates to pesticide precursor compositions comprising mustard bran and methods for using these compositions.

BACKGROUND OF THE INVENTION

Soil pests affect most cultivated crops and cause extensive damage, for example, to fruit crops, vegetables, cereals and ornamental plants, with resulting economic loss.

Efforts have been made to control soil pests by introducing pesticidal formulations onto or into the soil, before planting, at the time of planting or after planting. For example, the synthetic compound methyl isothiocyanate has been used as a soil fumigant against a variety of pests, including insects, nematodes, mites and various microorganisms.

In recent years, however, it has been realised that many of the pesticides currently in use are toxic and environmentally undesirable and there is a need to find practical alternatives which are more environmentally friendly.

Many Brassica species contain glucosinolates which can be converted by the endogenous plant enzyme myrosinase to a variety of compounds. For example, the glucosinolate sinigrin, which is found in mustards, can be converted by myrosinase to allyl isothiocyanate (AITC). As early as 1945, mustard oil and AITC were examined as a means of control of nematodes (Ellenby (1945), Annals of Applied Biol., v. 32, pp. 67-70; (1951), Annals of Applied Biol., v. 38, pp. 859-875).

Mustard oil did not, however, prove to be a practical pesticide for agricultural application due to its handling requirements, since it is an irritant liquid producing noxious fumes, and due to its immiscibility with soil moisture.

There remains a need for a practical and cost-effective treatment for soil pests which is at the same time environmentally- and user-friendly.

SUMMARY OF THE INVENTION

In the commercial preparation of mustard condiments, whole mustard seed is milled to strip off the outer seed coating or husk from the kernel or seed tissue. The kernel is ground into mustard flour which is sold as dry mustard condiment powder or is processed into other mustard condiments. The milled husk or bran is a waste product previously thought to have no commercial value and therefore discarded.

The present inventors have found, surprisingly, that mustard bran from some mustard species is a significant source of sinigrin and AITC and can be used as an inexpensive, effective and safely handled pesticide or soil fumigant, to control pests such as insects, nematodes, mites, fungi and bacteria.

Mustard bran can be applied to the soil in a manner similar to the application of a granular fertiliser. The mustard bran may be mixed with a suitable agricultural carrier to optimise its handling properties. On contact with water in the soil, the sinigrin of the mustard bran is converted by myrosinase from the bran to the active pesticide, AITC.

Mustard bran may also be used to prepare pesticidal aqueous extracts or aqueous suspensions which can be applied to pests or to the soil to achieve control.

In accordance with one embodiment of the present invention, there is provided a pesticide precursor composition comprising bran from a mustard of the genus Brassica.

In accordance with a further embodiment of the present invention, a method is provided for controlling a pest in soil which comprises applying to the soil an effective amount of a pesticide precursor composition comprising a bran from a mustard of the genus Brassica, wherein the bran contains an effective amount of sinigrin capable of conversion to allyl isothiocyaate on contact with water in the soil.

In accordance with a further embodiment of the invention, there is provided a pesticide comprising a pesticidally effective amount of an aqueous extract of bran from a mustard of the genus Brassica.

In accordance with a further embodiment of the invention, there is provided a pesticide comprising a pesticidally effective amount of an aqueous suspension of bran from a mustard of the genus Brassica.

In accordance with a further embodiment of the invention, a method is provided for controlling a pest which comprises applying to the pest an effective amount of an aqueous extract of bran from a mustard of the genus Brassica.

In accordance with a further embodiment of the invention, a method is provided for controlling a pest which comprises applying to the pest an effective amount of an aqueous suspension of bran from a mustard of the genus Brassica.

DETAILED DESCRIPTION OF THE INVENTION

The terms listed below have the following meanings:

"Mustard" means a species or a plant of the genus Brassica.

"Mustard condiment" means a food product or condiment prepared from a plant or from the seeds of a plant of the genus Brassica.

"Bran" or "mustard bran" means the husk or outer seed coating from the seeds of a plant of the genus Brassica removed from the kernel by milling or other suitable process.

Mustards with a high seed kernel concentration of sinigrin are valued for human consumption as seasonings and are used for the preparation of mustard condiments and other food products.

The mustard seed is first milled to remove the outer husk, typically by an abrasive process, and the kernel is ground into flour for condiment production. Until the work of the present inventors, the residual bran was considered a waste product and was discarded.

It has now been shown that mustard bran can be a useful and effective pesticide precursor, providing sinigrin and myrosinase. Under moist conditions, the sinigrin is converted by the myrosinase to the pesticidal compound, AITC.

This is exemplified in Example 2 in which aqueous extracts of mustard bran were compared with extracts of mustard flour, which is known to contain high levels of sinigrin, with respect to nematicidal activity. Bran was found to have excellent nematicidal activity. In contrast, extracts of whole mustard seed or cracked mustard seed showed very low nematicidal activity.

In accordance with one embodiment of the invention, a method is provided for controlling soil pests by applying a pesticide precursor composition comprising mustard bran to the soil.

Mustard bran may be applied to the soil in a similar manner to the application of materials such as granular fertilisers and using similar commercially available agricultural equipment. For example, the bran may be scattered on the soil surface or incorporated into the soil with a disk or rototiller. Application may be prior to planting, at the time of planting or after planting, as desired.

In accordance with a further embodiment of the invention, mustard bran may be mixed with an agriculturally acceptable carrier to improve its handling properties before application to the soil. Those skilled in the art will be familiar with carrier materials which are suitable for formulation of pesticidal compositions for application to soil. Such carriers include finely ground clay, starch-based or plastic polymers, surfactants or organic carriers such as ground corn cobs.

Cracked mustard seed may also be used as a carrier. Lower grade mustard seed of insufficient quality for processing into flour for condiment preparation may be employed for this purpose.

In accordance with a further embodiment, mustard bran may be formulated with a mixture of carriers, and optionally may be formulated in a variety of forms; for example, it may be formulated into layered granules, to obtain a desired rate of release of pesticide into the soil. Such methods of formulation are known to those skilled in the art.

Mustard bran is an environmentally friendly pesticide, being a natural and biodegradable product.

It is also much more easily and safely handled than pesticides such as synthetic methyl isothiocyanate, as the dry bran is non-toxic and the effective pesticide, the irritant and toxic compound AITC, is formed from the sinigrin contained in the bran only after application of the composition to the soil and its contact with water in the soil.

The dry bran may be formulated, handled and applied without the precautions which would be required for dealing with AITC.

In accordance with a further embodiment of the invention, a pesticide comprising an aqueous extract or an aqueous suspension of mustard bran may be prepared and applied to pests or to the soil to achieve pest control. Application may be carried out, for example, by spraying the suspension or extract on the pests or on to the soil.

As will be understood by those skilled in the art, mustard bran effective as a pesticide precursor may be obtained from any Brassica species or variety having a husk sinigrin content sufficient to give a desired level of pest control on conversion to AITC. As exemplified herein, a mustard having a sinigrin content of about 2.5% by weight provides an effective level of pesticide activity. Sinigrin may be measured by a standard technique, such as those described by Minchinton, I. et al., (1982), J. Chromatog., v. 247, pp. 141–148; Sang, J. P. et al., (1984), Can. J. Plant.Sci., v. 64, pp. 77–93; Betz, J. M. and Fox, W. D., (1994), in "Food Phytochemicals for Cancer Prevention", ACS Symposium Series 546, American Chemical Society, pp. 181–193.

Mustards having a higher or lower husk sinigrin content may also be employed in the pesticide precursor compositions of the invention. It is within the expertise of those skilled in the art to determine whether the bran from any variety of mustard is effective to give a desired level of pest control.

Suitable Brassica varieties may be found, for example, in the following species:

Brassica juncea;

Brassica campestris; and

Brassica nigra.

Brassica juncea, cv Forge and Brassica juncea. cv Cutlass are preferred varieties of B. juncea.

Brassica species or varieties may also be bred or genetically engineered to increase husk content of sinigrin. Brassicas such as Brassica napus have already been shown to be amenable to successful genetic manipulation to improve various properties. Such techniques may be used to convert species or varieties with naturally low husk sinigrin content to a useful level or may be used to further enhance husk sinigrin in high-sinigrin varieties. Transgenic or hybrid Brassicas so produced may also be used in the compositions of the invention.

As AITC is believed to act against pests by a similar mechanism to that of methyl isothiocyanate, the pesticide precursor compositions and pesticides of the invention can be expected to combat a similar range of pests, including plant-parasitic nematodes, insects, mites, fungi and bacteria.

The following examples are described for the purpose of illustration and are not intended to limit the scope of the invention.

EXAMPLE 1

Samples of mustard bran and mustard flour from various mustard types were obtained from a commercial mustard milling company.

Sinigrin content was determined by extracting a portion of bran or flour in phosphate buffer, pH 7.0, at 100° C. for 20 min. The aqueous extract was purified by chromatography on a C18-solid phase extraction cartridge and the purified sinigrin was determined by high performance liquid chromatography.

The available AITC was calculated as 23.9% of the sinigrin concentration, on the basis of the relative molecular weights and the demonstrated quantitative conversion of sinigrin to AITC by myrosinase (data not shown).

The results are shown in Table 1.

TABLE 1

| Mustard Variety | Sinigrin Conc. (mg/g) | | AITC Conc. (mg/g) | |
| --- | --- | --- | --- | --- |
| | Bran | Flour | Bran | Flour |
| Oriental[a] | 25.2 | 40.2 | 6.0 | 9.6 |
| Yellow[b] | nd | 1.9 | nd | 0.5 |
| Mixed[c] | 9.3 | 24.7 | 2.2 | 5.9 |

[a]Brassica juncea, cv. Forge (Oriental mustard)
[b]Brassica napus (Yellow mustard or rapeseed)
[c]Mixture of Oriental and Yellow mustard
nd = not detected

EXAMPLE 2

Nematicidal efficacy of various mustard-derived materials was determined using aqueous extracts of the materials applied to the lesion nematode Pratylenchus penetrans. Materials extracted were from Brassica juncea cv. Forge, as follows:

1. Intact seed.
2. Cracked seed.
3. Mustard bran.
4. Mustard flour.
5. Formulated bran: 1 g mustard bran was mixed well with 1.5 g canola oil. After 30 minutes, 2.5 g powdered clay was added and the mixture was mixed well in a mortar.
6. Formulated bran: bran was formulated as in 5, except that Tween-20 was used instead of canola oil.

Weighed portions of each sample were extracted with 50 ml water at room temperature, either for 30 mins or 60 mins, and filtered. A 1 ml portion of each filtered aqueous extract was mixed with 2 ml of a suspension of *Pratylenchus penetrans* (100 or 200 nematodes per 2 ml) and the nematodes were assessed for mobility and mortality at various intervals. Mobility was assessed by microscopic observation. Mortality was determined after 68–72 hours of exposure to the extracts by looking for lack of movement on visual inspection and no reaction to mechanical stimulation.

The results are shown in Tables 2 (30 minute extraction) and 3 (60 minute extraction).

TABLE 2

| Sample Number | Weight of sample extracted | Mobility 2 hrs. | % Mobility- 4 hrs. treatment | % Mortality 68–72 hrs. |
|---|---|---|---|---|
| 1 | 231 | all active | 100.0 | 10.0 |
| 2 | 231 | most inactive | 4.4 | 14.1 |
| 3 | 301 | ", sluggish | 1.3 | 45.8 |
| 4 | 189 | slight movement | 5.1 | 54.9 |
| 5 | 1506 | slight movement | 1.4 | 51.6 |
| 6 | 1506 | slight movement | 11.4 | 46.0 |

TABLE 3

| Sample Number | Weight of sample extracted | Nematode Mobility- 2 hrs. treatment | % Mobility- 4 hrs. treatment | % Mortality 68–72 hrs. |
|---|---|---|---|---|
| 1 | 231 | all active | 100.0 | 2.7 |
| 2 | 231 | slight movement | 3.6 | 4.0 |
| 3 | 301 | slight movement | 12.5 | 84.5 |
| 4 | 189 | slight movement | 15.8 | 72.8 |
| 5 | 1506 | slightly more than above | 5.7 | 69.3 |
| 6 | 1506 | slightly more than above | 13.4 | 69.1 |

Although only preferred embodiments of the present invention have been described, the present invention is not limited to the features of these embodiments, but includes all variations and modifications within the scope of the claims.

We claim:

1. A method for controlling plant-parasitic nematodes or fungi in soil, which method comprises applying to the soil a pesticide precursor composition comprising a bran from a mustard of the genus Brassica, wherein the bran is separated from mustard seed, wherein the bran contains sinigrin capable of conversion to allyl isothiocyanate on contact with water in the soil, and further wherein the pesticide precursor composition is applied in an amount sufficient to provide an amount of allyl isothiocyanate pesticidally effective against said plant parasitic nematodes or fungi on contact with water in the soil.

2. The method of claim 1 wherein the composition further comprises an agriculturally acceptable carrier.

3. The method of claim 2 wherein the bran is from a mustard of a species selected from the group consisting of
   (a) *Brassica juncea;*
   (b) *Brassica campestris;* and
   (c) *Brassica nigra.*

4. The method of claim 2 wherein the bran is from a mustard of the species *Brassica juncea.*

5. The method of claim 4 wherein the mustard is of the variety *B. juncea* cv. Forge or *B. juncea* cv. Cutlass.

6. The method of claim 4 wherein the carrier comprises cracked mustard seed.

7. The method of claim 4 wherein the carrier is selected from the group consisting of finely ground clay, at least one polymer, at least one surfactant and at least one organic carrier.

8. The method of claim 4 for controlling plant-parasitic nematodes in soil.

9. A method for controlling plant-parasitic nematodes or fungi, which comprises applying thereto an aqueous extract of bran from a mustard of the genus Brassica, wherein the bran is separated from mustard seed, in an amount sufficient to provide an amount of allyl isothiocyanate pesticidally effective against said plant parasite nematodes or fungi.

10. A method for controlling plant-parasitic nematodes or fungi, which comprises applying thereto an aqueous suspension of bran from a mustard of the genus Brassica, wherein the bran is separated from mustard seed, in an amount sufficient to provide an amount of allyl isothiocyanate pesticidally effective against said plant parasite nematodes or fungi.

* * * * *